United States Patent [19]
Takemoto et al.

[11] Patent Number: 5,990,324
[45] Date of Patent: Nov. 23, 1999

[54] PROCESS FOR PRODUCING 3-METHYLTETRAHYDROFURAN

[75] Inventors: Masaki Takemoto; Takafumi Abe, both of Niigata-ken, Japan

[73] Assignee: Mitsubishi Gas Chemical Company, Inc., Tokyo, Japan

[21] Appl. No.: 09/039,954

[22] Filed: Mar. 16, 1998

[30] Foreign Application Priority Data

Apr. 2, 1997 [JP] Japan .................................... 9-083865

[51] Int. Cl.$^6$ ................................................. C07D 307/06
[52] U.S. Cl. ............................................................ 549/508
[58] Field of Search ............................................. 549/508

[56] References Cited

U.S. PATENT DOCUMENTS 5,478,952 12/1995 Schwartz ................................. 549/325

FOREIGN PATENT DOCUMENTS

| | | |
|---|---|---|
| 0 343 985 A2 | 11/1989 | European Pat. Off. . |
| 0 589 314 A1 | 3/1994 | European Pat. Off. . |
| 63-235320 | 9/1988 | Japan . |
| 6-219981 | 9/1994 | Japan . |
| 8-217768 | 8/1996 | Japan . |

*Primary Examiner*—Bernard Dentz
*Attorney, Agent, or Firm*—Frishauf, Holtz, Goodman, Langer & Chick, P.C.

[57] ABSTRACT

There is disclosed a process for producing 3-methyltetrahydrofuran which comprises the step 1 of subjecting the compound represented by the general formula [I]

$$ROOC\text{—}CH(CH_3)\text{—}CH_2\text{—}CHO \qquad [I]$$

wherein R is an alkyl group having 1 to 3 carbon atoms and the formyl group may be present as an acetal having an alkanol with 1 to 8 carbon atoms, to hydrogenation and alcohol-eliminating cyclization to synthesize 2-methyl-γ-butyrolactone; the step 2 of separating the 2-methyl-γ-butyrolactone formed in the step 1 from alcohols by means of distillation, etc.; and the step 3 of hydrogenating the 2-methyl-γ-butyrolactone which is formed in the step 2. The above process enables the production of the objective highly-pure 3-methyltetrahydrofuran substantially free from an alcohol in high efficiency and high conversion through simplified production steps.

17 Claims, No Drawings

PROCESS FOR PRODUCING 3-METHYLTETRAHYDROFURAN

BACKGROUND OF THE INVENTION

1. Field of the Invention

The present invention relates to a process for producing 3-methyltetrahydrofuran, which is an extremely useful substance that is utilized as a comonomer for modifying poly(tetramethylene ether glycol) obtained by polymerizing tetrahydrofuran. [Refer to Japanese Patent Application Laid-Open No. 235320/1988 (Sho-63) and European Patent Application Laid-Open No. 343985].

2. Description of the Related Arts

As a process for producing 3-methyltetrahydrofuran, Japanese Patent Application Laid-Open No. 219981/1994 (Hei-6) describes the process for producing 2-methyl-1,4-butane-diol and 3-methyltetrahydrofuran by the hydrogenation of an itaconic acid ester or a 3-formyl-2-methylpropionic acid ester, and also Japanese Patent Application Laid-Open No. 217768/1996 (Hei-8) describes the process for producing 3-methyltetrahydrofuran by the hydrogenation of a methyl-succinic acid ester. However, when an attempt is made to produce 3-methyltetrahydrofuran by the use of the above-mentioned ester as a starting raw material, it is inevitable that the reaction product contains an alcohol as well as the objective 3-methyltetrahydrofuran. 3-Methyltetrahydrofuran forms an azeotropic mixture with most of the lower alcohols, for example, with methanol, forming an azeotropic mixture having an azeotropic point of 64.5° C. and an azeotropic composition consisting of 25% by weight of 3-methyltetrahydrofuran and 75% by weight of methanol, thus it requires a large amount of energy to separate 3-methyltetrahydrofuran from the azeotropic mixture. In particular, the 3-methyltetrahydro-furan which is employed for modifying poly(tetramethylene glycol) is required to have highly purity and to have contents of alcohols not more than 0.2%

SUMMARY OF THE INVENTION

The object of the present invention is to provide an effective process for producing 3-methyltetrahydrofuran free from an alcohol which is difficult to separate by an ordinary distillation procedure.

Under such circumstances, intensive research and investigation were carried out by the present inventors in order to solve the foregoing problems. As a result, it has been found that 3-methyltetrahydrofuran free from an alcohol can efficiently be produced by a process which comprises the step 1 of subjecting the compound represented by the general formula [I]

ROOC—CH (CH$_3$)—CH$_2$—CHO   [I]

wherein R is an alkyl group having 1 to 3 carbon atoms and the formyl group may be present as an acetal having an alkanol with 1 to 8 carbon atoms, to hydrogenation and alcohol-removing cyclization to synthesize 2-methyl-γ-butyrolactone; the step 2 of separating the 2-methyl-γ-butyrolactone formed in the step 1 from alcohols by means of distillation or the like; and the step 3 of hydrogenating the alcohol-free 2-methyl-γ-butyrolactone formed in the step 2. The present invention has been accomplished by the foregoing findings and information.

DESCRIPTION OF PREFERRED EMBODIMENTS

In the following, the process according to the present invention will be described in detail with reference to the chemical equations of the process for producing 3-methyltetrahydrofuran.

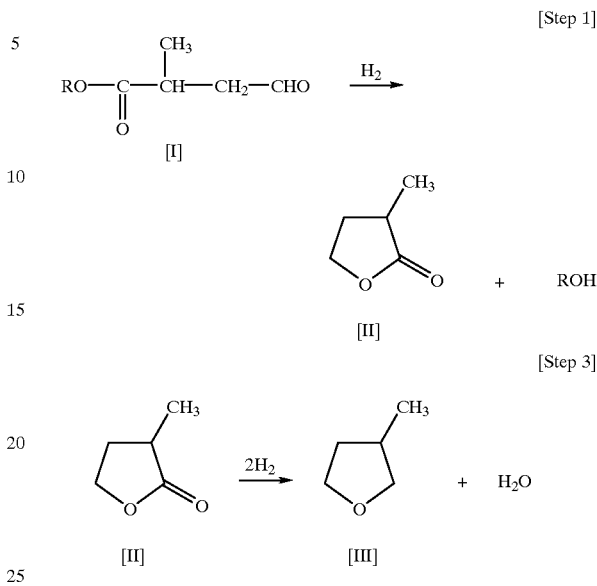

wherein [I] is a β-formylisobutyric acid ester, [II] is 2-methyl-γ-butyrolactone, [III] is 3-methyltetrahydrofuran, R is an alkyl group having 1 to 3 carbon atoms and the formyl group may be present as an acetal having an alkanol with 1 to 8 carbon atoms.

The process according to the present invention is characterized in that two-stage hydrogenation reaction is effected, that is, in the hydrogenation reaction of the compound [I], the compound [I] is not directly hydrogenated to the objective 3-methyltetrahydrofuran (compound [III]), but is stopped at the stage of 2-methyl-γ-butyrolactone (compound [II]) as an intermediate to separate, in this stage, alcohols that cause problems in the purification of 3-methyltetrahydrofuran; and further the alcohol-free 2-methyl-γ-butyrolactone is hydrogenated. The compound [I] as the starting raw material can be obtained in high yield and high selectivity by the hydroformylation of a methacrylic acid ester [refer to Bull. Chem. Soc. Japan 50 (1977) 2351)].

It is the key factor in the hydrogenation reaction of the step 1 of the process according to the present invention not to hydrogenate the β-formylisobutyric acid ester directly to 3-methyltetrahydrofuran, but to stop it at the stage of 2-methyl-γ-butyrolactone. The above-mentioned aim is easily attainable provided that excessively severe reaction conditions are avoided, since it is normally easier to proceed with the hydrogenation reaction of a formyl group by a metal catalyst than that of an ester group , and it is quite easy to proceed with the alcohol-eliminating cyclization of 4-hydroxy-2-methylbutyric acid ester which is formed by the above-mentioned reaction.

The catalyst to be used in the hydrogenation reaction of the step 1 of the process according to the present invention comprises a compound containing, as a principal component, copper, or a metal belonging to the group 7 a or 8 of the Periodic Table. In more detail, it is effective to use any of copper, cobalt, nickel, iron, rhenium, palladium, ruthenium, platinum and rhodium as a principal component of the catalyst. In addition, it is effective to employ any component of chromium, molybdenum, manganese, barium, magnesium and a solid acid containing silicon or aluminum as a promoter. A preferred catalyst is for example copper-chromite. It is possible to adopt in the hydrogenation reaction of the step 1, a suspended bed system, trickle bed system or cocurrent vapor-liquid uprise system. However, the reaction process is not limited in particular.

Although depending upon the catalyst component to be used, the hydrogenation reaction of the step 1 of the process according to the present invention is put into practice usually under a reaction temperature in the range of 50 to 200° C. and a reaction pressure in the range of atmospheric pressure to 100 kg/cm$^2$ G (gauge pressure). As an example, in the case of employing a catalyst called copper-chromite which comprises copper as a principal ingredient, it is preferable that the reaction temperature be in the range of 70 to 180° C. and a reaction pressure be in the range of 5 to 40 kg/cm$^2$ G. The hydrogen to be used for the hydrogenation reaction is preferably pure hydrogen, but the hydrogen containing methane, nitrogen and the like may also be used.

The separation of the 2-methyl-γ-butyrolactone from alcohols in the step 2 of the process according to the present invention can easily be carried out by an ordinary distillation procedure, which however shall not limit the separation method thereto.

The hydrogenation reaction of the 2-methyl-γ-butyrolactone free from alcohols in the step 3 of the process according to the present invention is put into practice in the presence of a catalyst comprising a compound containing as a principal component, copper, or a metal belonging to the group 7 a or 8 of the Periodic Table. In more detail, it is effective to use any of copper, cobalt, nickel, iron, rhenium, palladium, ruthenium, platinum and rhodium as a principal component of the catalyst. In addition, it is effective to employ any component of chromium, molybdenum, manganese, barium, magnesium and a solid acid containing silicon or aluminum as a promoter. A preferred catalyst is for example copper-chromite. It is possible to adopt in the hydrogenation reaction of this step 3, a suspended bed system, trickle bed system or cocurrent vapor-liquid uprise system. However, the reaction process is not limited in particular. The reaction mixture obtained by the above-mentioned procedure is separated and purified by ordinary distillation procedure to afford 3-methyltetrahydrofuran as the objective product.

Although depending upon the the catalyst component to be used, the hydrogenation reaction of the step 3 of the process according to the present invention is put into practice usually under a reaction temperature in the range of 50 to 300° C. and a reaction pressure in the range of atmospheric pressure to 200 kg/cm$^2$ G (gauge pressure). As an example, in the case of employing a catalyst called copper-chromite which comprises copper as a principal ingredient, it is preferable that the reaction temperature be in the range of 150 to 250° C. and a reaction pressure be in the range of 50 to 150 kg/cm$^2$ G. The hydrogen to be used for hydrogenation reaction is preferably pure, but hydrogen containing methane, nitrogen and the like may also be used.

According to the present invention, it is made possible to produce highly pure 3-methyltetrahydrofuran substantially free from an alcohol by the use of methyl β-formylisobutyrate as a starting raw material through the three extremely straightforward steps, thereby rendering the present process highly valuable from the industrial point of view.

In the following, the present invention will be described in more detail with reference to working examples, which however shall not limit the present invention thereto.
[Step 1]
Example 1

In a 20 ml stainless steel-made autoclave as a reactor equipped with a thermometer and a pressure indicator, were charged 0.1 g of copper-chromite as the catalyst (produced by Nissan Girdler Catalyst Co., Ltd. under the trade name: G-99C in the form of powder ) and 3.5 g of m-xylene as a solvent. After the atmosphere in the reactor was sufficiently replaced with hydrogen, the reactor was charged with hydrogen up to 20 kg/cm$^2$ G and was immersed in an oil bath maintained at 200° C., and the reactant liquid in the reactor was stirred by means of a magnetic stirrer for 30 minutes to reduce the catalyst. Subsequently, the reactor was cooled and the hydrogen gas therein was purged, and thereafter 1.5 g of methyl β-formylisobutyrate was fed thereinto. After the atmosphere in the reactor was sufficiently replaced with hydrogen, the reactor was charged with hydrogen up to 20 kg/cm$^2$ G and was immersed in an oil bath maintained at 150° C., and the reactant liquid in the reactor was stirred by means of a magnetic stirrer for 2 hours to proceed with the reaction. The reaction pressure reached 22 kg/cm$^2$ G after 10 minutes from the start of the temperature rise and was 13 kg/cm$^2$ G at the time when the reaction was completed. As the result of analysis of the reaction liquid by gas chromatography, the objective 2-methyl-γ-butyrolactone was obtained in a yield of 94.9% in a methanol yield of 91.2% at a conversion efficiency of methyl β-formylisobutyrate of 100%, accompanied by the formation of methyl 3-hydroxy-isovalerate in a yield of 3.2%
Example 2

The procedure in Example 1 was repeated to proceed with the reaction except that 0.1 g of nickel-diatomaceous earth (produced by Nikki Chemical Co. Ltd . under the trade name N-113 in the form of powder) was used as the catalyst in place of the copper-chromite. As the result of analysis of the reaction liquid by gas chromatography, the objective 2-methyl-γ-butyrolactone was obtained in a yield of 95.6% in a methanol yield of 90.7% at a conversion efficiency of methyl β-formylisobutyrate of 100%, while forming methyl 3-hydroxyisovalerate in a yield of 1.9% and 3-methyltetrahydrofuran in a yield of 0.6% .
[Step 2]
Example 3

The reaction liquid which had been formed in Example 1 was fractionated into each of the components by means of distillation equipment which was equipped with a fractionation section having an inside diameter of 15 mm and a length of 500 mm and which was packed inside with 3 mm Dickson packings. The objective 2-methyl-γ-butyrolactone having a purity of at least 99% was recovered in a yield of 90 mol % based on the methyl β-formylisobutyrate which had been used as the starting raw material in Step 1.
[Step 3]
Example 4

A stainless steel-made tubular reactor to be used as a hydrogenation reactor having an inside diameter of 15 mm and a length of 300 mm was packed inside with 10 g of copper-chromite as the catalyst roughly uniformized in particle size of 10 to 20 mesh ( produced by Nissan Girdler Catalyst Co.,Ltd. under the trade name: G-99C in the form of pellets). Subsequently, a catalyst reduction was carried out at 150 to 200° C. by passing through the reactor, hydrogen gas diluted with nitrogen to 0.5 to 5% by volume by the conventional method with sufficient care not to form a hot spot. Thereafter, the feed gas to the reactor was switched to pure hydrogen at a pressure of 70 kg/cm$^2$ G, a purge gas SV of 500 hr$^{-1}$ and a catalyst bed temperature of 230° C. Then, the tubular reactor was charged at an upper portion thereof with a starting material for reaction consisting of a solution of 30 parts by weight of 2-methyl-γ-butyrolactone which had been obtained in Example 3 in 70 parts by weight of m-xylene at a rate of 3.3 g per hour. The effluent through a lower portion thereof was cooled and degasified to collect the reaction product. After the lapse of 5 hours from the start of the reaction, the reaction product was collected for one hour and analyzed by gas chromatography. As a result, the objective 3-methyltetrahydrofuran was obtained in a yield of 90.1% in a conversion efficiency of 2-methyl-γ-butyro-lactone of 100% in a yield of 0.5% methyl isobutyrate, while methanol was not detected in the reaction product throughout the reaction period.

What is claimed is:

1. A process for producing 3-methyltetrahydrofuran which comprises (a) subjecting the compound represented by the formula (I)

ROOC—CH(CH$_3$)—CH$_2$-X     (I)

wherein R is an alkyl group having 1 to 3 carbon atoms and X is a formyl group or an acetal having an alkanol with 1 to 8 carbon atoms, to hydrogenation and alcohol-removing cyclization to synthesize 2-methyl-γ-butyrolactone;

(b) separating the 2-methyl-γ-butyrolactone formed in step (a) from alcohols; and (c) hydrogenating the 2-methyl-γ-butyrolactone which is separated in step (b).

2. The process for producing 3-methyltetrahydrofuran according to claim 1, wherein the compound represented by the formula (I) is a compound which is produced by the hydroformylation reaction of a methacrylic acid ester.

3. The process for producing 3-methyltetrahydrofuran according to claim 1, wherein the compound represented by the formula (I) is methyl β-formylisobutyrate.

4. The process for producing 3-methyltetrahydrofuran according to claim 1, wherein the hydrogenation reaction in any of the step (a) and step (c), is effected in the presence of at least one member selected from the group consisting of copper, copper compounds, metals of the group 7 a, metals of the group 8, compounds of a metal of the group 7 a, and compounds of a metal of the group 8.

5. The process for producing 3-methyltetrahydrofuran according to claim 1, wherein the hydrogenation reaction in any of the step (a) and step (c), is effected in the presence of copper-chromite as a catalyst.

6. The process for producing 3-methyltetrahydrofuran according to claim 1, wherein the 2-methyl-γ-butyrolactone is separated from alcohols by distillation.

7. The process for producing 3-methyltetrahydrofuran according to claim 1, wherein the resultant 3-methyltetrahydrofuran is substantially free from an alcohol.

8. The process for producing 3-methyltetrahydrofuran according to claim 1, wherein X is a formyl group.

9. The process for producing 3-methyltetrahydrofuran according to claim 1, wherein X is an acetal having an alkanol with 1 to 8 carbon atoms.

10. The process for producing 3-methyltetrahydrofuran according to claim 1, wherein the hydrogenation in at least one of steps (a) and (c) is carried out in the presence of a catalyst comprising a compound including a metal selected from the group consisting of copper, cobalt, nickel, iron, rhenium, palladium, ruthenium, platinum and rhodium.

11. The process for producing 3-methyltetrahydrofuran according to claim 10, wherein the hydrogenation in step (a) is carried out at a temperature of 50 to 200° C. and at a pressure of atmospheric to 100 kg/cm$^2$G.

12. The process for producing 3-methyltetrahydrofuran according to claim 11, wherein the temperature is 70 to 180° C. and the pressure is 5 to 40 kg/cm$^2$G.

13. The process for producing 3-methyltetrahydrofuran according to claim 12, wherein the hydrogenation in step (c) is carried out at a temperature of 50 to 300° C. and at a pressure of atmospheric to 200 kg/cm$^2$G.

14. The process for producing 3-methyltetrahydrofuran according to claim 13, wherein the hydrogenation in step (c) is carried out at a temperature of 150 to 250° C. and at a pressure of 50 to 150 kg/cm$^2$G.

15. The process for producing 3-methyltetrahydrofuran according to claim 14, wherein the compound represented by the formula (I) is methyl-β-formylisobutyrate.

16. The process for producing 3-methyltetrahydrofuran according to claim 15, wherein the hydrogenation in step (a) is carried out with copper-chromite as the catalyst.

17. The process for producing 3-methyltetrahydrofuran according to claim 16, wherein the hydrogenation in step (c) is carried out with copper-chromite as the catalyst.

* * * * *